(12) United States Patent
Yokoi et al.

(10) Patent No.: US 6,893,848 B1
(45) Date of Patent: May 17, 2005

(54) DESENSITIZED ASPARTOKINASE

(75) Inventors: Haruhiko Yokoi, Yokohama (JP); Junko Ohnishi, Machida (JP); Keiko Ochiai, Ebina (JP); Yoshiyuki Yonetani, Machida (JP); Akio Ozaki, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/958,606

(22) PCT Filed: Apr. 14, 2000

(86) PCT No.: PCT/JP00/02456
§ 371 (c)(1),
(2), (4) Date: Feb. 6, 2002

(87) PCT Pub. No.: WO00/63388
PCT Pub. Date: Oct. 26, 2000

(30) Foreign Application Priority Data

Apr. 19, 1999 (JP) ............................................. 11/110437

(51) Int. Cl.[7] ......................... C07C 229/00; C12N 1/20; C12N 15/63; C12N 9/12; C12N 15/74; C07N 21/04; C12P 13/08

(52) U.S. Cl. ..................... 435/115; 435/252.3; 435/194; 435/320.1; 435/252.32; 435/471; 435/478; 536/23.2; 562/562

(58) Field of Search ....................... 562/562; 536/23.2; 435/252.3, 194, 320.1, 252.32, 471, 478, 115

(56) References Cited

U.S. PATENT DOCUMENTS

| | | | |
|---|---|---|---|
| 3,708,395 A | 1/1973 | Nakayama et al. | 195/29 |
| 4,623,623 A | 11/1986 | Nakanishi et al. | 435/115 |
| 4,657,860 A | 4/1987 | Nakanishi et al. | 435/115 |
| 5,236,831 A | 8/1993 | Katsumata et al. | 435/106 |
| 5,688,671 A | 11/1997 | Sugimoto et al. | 435/115 |

FOREIGN PATENT DOCUMENTS

| | | |
|---|---|---|
| EP | 259858 | 3/1988 |
| EP | 0 699 759 | 3/1996 |
| JP | 59-88094 | 5/1984 |
| JP | 63-62199 | 12/1988 |
| JP | 5-11959 | 2/1993 |
| JP | 5-5514 | 8/1993 |
| JP | 6-62866 | 3/1994 |
| JP | 6-261766 | 9/1994 |
| JP | 7-55155 | 6/1995 |
| WO | 94/25605 | 11/1994 |

OTHER PUBLICATIONS

"Amino Acid Fermentation", Japan Scientific Societies Press (1986), p273 (with partial English translation).

Follettie, et al., "Gene Structure and Expression of the Corynebacterium", Journal of Bacteriology, vol. 175, No. 13 (1993), pp. 4096–4103.

Kalinowski, et al., "Genetic and biochemical analysis of the . . . ", Molecular Microbiology, vol. 5, No. 5 (1991), pp. 1197–1204.

Enei, et al., "Recent Progress in Microbial Production of Amino Acids" (1989), pp. 47–53.

Leuchtenberger, "Amino–Acids—Technical Production and Use", pp. 474–482.

Primary Examiner—Rebecca E. Prouty
Assistant Examiner—Sheridan L. Swope
(74) Attorney, Agent, or Firm—Fitzpatrick, Cella, Harper & Scinto

(57) ABSTRACT

The present invention relates to a novel aspartokinase derived from a Coryneform bacterium; a DNA encoding the enzyme; a recombinant DNA containing the above DNA; a Coryneform bacterium having the above recombinant DNA or a Coryneform bacterium having the DNA on its chromosome; and a process for producing L-lysine by culturing the above microorganism. Construction has been successfully made of a DNA encoding an aspartokinase freed from concerted feedback inhibition by L-lysine and L-threonine derived from a *Corynebacterium* and has a nucleotide sequence encoding an amino acid sequence wherein the amino acid residue at position 311 is an amino acid other than Thr in the amino acid sequence shown by SEQ ID NO: 18.

15 Claims, 1 Drawing Sheet

SEQUENCE LISTING

```
<160> NUMBER OF SEQ ID NOS: 18

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 1
aaaaagatct cgacggatcg ttccactg                                           28

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 2
gtaaaacgac ggccatg                                                       17

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 3
cgagtcgact cgcgaagtag cacctgtcac ttttg                                   35

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 4
tggggatccg caccaacaac tgcgatggtg gtc                                     33

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence : Synthetic
      DNA
```

```
<400> SEQUENCE: 5
aaaactcgag aggtctgcct cgtg                                          24

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 6
caggaaacag ctatgac                                                  17

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 7
tgcagcggca gtgaatcccg ttccgcc                                       27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 8
ttctgacacc actgcagttg cgttgg                                        26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 9
tcgcaaccga caagtccgaa gccaaag                                       27

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 10
tgaagtctca cccaggtgtt accgcagag                                     29

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence : Synthetic
      DNA
```

```
<400> SEQUENCE: 11
caagggactc aatagcgatg gcgacgag                                          28

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 12
cagcaacttc cagcatttct tcgaagc                                           27

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 13
gcatcccagt ggctgagacg catccgcta                                         29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 14
ctgcgatggt ggtcattgta aaactactcc                                        30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 15
catcgcgcag agcttccatg aactctgcgg                                        30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 16
gggatcatta ctataagacg agcgtacgcg                                        30

<210> SEQ ID NO 17
<211> LENGTH: 1263
<212> TYPE: DNA
<213> ORGANISM: Corynebacterium glutamicum
<220> FEATURE:
<221> NAME/KEY: CDS
<222> LOCATION:

<400> SEQUENCE: 17
```

-continued

| | |
|---|---|
| gtg gcc ctg gtc gta cag aaa tat ggc ggt tcc tcg ctt gag agt gcg<br>Val Ala Leu Val Val Gln Lys Tyr Gly Gly Ser Ser Leu Glu Ser Ala<br>1               5                   10                  15 | 48 |
| gaa cgc att aga aac gtc gct gaa cgg atc gtt gcc acc aag aag gct<br>Glu Arg Ile Arg Asn Val Ala Glu Arg Ile Val Ala Thr Lys Lys Ala<br>            20                  25                  30 | 96 |
| gga aat gat gtc gtg gtt gtc tgc tcc gca atg gga gac acc acg gat<br>Gly Asn Asp Val Val Val Val Cys Ser Ala Met Gly Asp Thr Thr Asp<br>        35                  40                  45 | 144 |
| gaa ctt cta gaa ctt gca gcg gca gtg aat ccc gtt ccg cca gct cgt<br>Glu Leu Leu Glu Leu Ala Ala Ala Val Asn Pro Val Pro Pro Ala Arg<br>50                  55                  60 | 192 |
| gaa atg gat atg ctc ctg act gct ggt gag cgt att tct aac gct ctc<br>Glu Met Asp Met Leu Leu Thr Ala Gly Glu Arg Ile Ser Asn Ala Leu<br>65                  70                  75                  80 | 240 |
| gtc gcc atg gct att gag tcc ctt ggc gca gaa gcc caa tct ttc acg<br>Val Ala Met Ala Ile Glu Ser Leu Gly Ala Glu Ala Gln Ser Phe Thr<br>                85                  90                  95 | 288 |
| ggc tct cag gct ggt gtg ctc acc acc gag cgc cac gga aac gca cgc<br>Gly Ser Gln Ala Gly Val Leu Thr Thr Glu Arg His Gly Asn Ala Arg<br>            100                 105                 110 | 336 |
| att gtt gat gtc act cca ggt cgt gtg cgt gaa gca ctc gat gag ggc<br>Ile Val Asp Val Thr Pro Gly Arg Val Arg Glu Ala Leu Asp Glu Gly<br>        115                 120                 125 | 384 |
| aag atc tgc att gtt gct ggt ttc cag ggt gtt aat aaa gaa acc cgc<br>Lys Ile Cys Ile Val Ala Gly Phe Gln Gly Val Asn Lys Glu Thr Arg<br>130                 135                 140 | 432 |
| gat gtc acc acg ttg ggt cgt ggt ggt tct gac acc act gca gtt gcg<br>Asp Val Thr Thr Leu Gly Arg Gly Gly Ser Asp Thr Thr Ala Val Ala<br>145                 150                 155                 160 | 480 |
| ttg gca gct gct ttg aac gct gat gtg tgt gag att tac tcg gac gtt<br>Leu Ala Ala Ala Leu Asn Ala Asp Val Cys Glu Ile Tyr Ser Asp Val<br>                165                 170                 175 | 528 |
| gac ggt gtg tat acc gct gac ccg cgc atc gtt cct aat gca cag aag<br>Asp Gly Val Tyr Thr Ala Asp Pro Arg Ile Val Pro Asn Ala Gln Lys<br>            180                 185                 190 | 576 |
| ctg gaa aag ctc agc ttc gaa gaa atg ctg gaa ctt gct gct gtt ggc<br>Leu Glu Lys Leu Ser Phe Glu Glu Met Leu Glu Leu Ala Ala Val Gly<br>        195                 200                 205 | 624 |
| tcc aag att ttg gtg ctg cgc agt gtt gaa tac gct cgt gca ttc aat<br>Ser Lys Ile Leu Val Leu Arg Ser Val Glu Tyr Ala Arg Ala Phe Asn<br>210                 215                 220 | 672 |
| gtg cca ctt cgc gta cgc tcg tct tat agt aat gat ccc ggc act ttg<br>Val Pro Leu Arg Val Arg Ser Ser Tyr Ser Asn Asp Pro Gly Thr Leu<br>225                 230                 235                 240 | 720 |
| att gcc ggc tct atg gag gat att cct gtg gaa gaa gca gtc ctt acc<br>Ile Ala Gly Ser Met Glu Asp Ile Pro Val Glu Glu Ala Val Leu Thr<br>                245                 250                 255 | 768 |
| ggt gtc gca acc gac aag tcc gaa gcc aaa gta acc gtt ctg ggt att<br>Gly Val Ala Thr Asp Lys Ser Glu Ala Lys Val Thr Val Leu Gly Ile<br>            260                 265                 270 | 816 |
| tcc gat aag cca ggc gag gct gcg aag gtt ttc cgt gcg ttg gct gat<br>Ser Asp Lys Pro Gly Glu Ala Ala Lys Val Phe Arg Ala Leu Ala Asp<br>        275                 280                 285 | 864 |
| gca gaa atc aac att gac atg gtt ctg cag aac gtc tct tct gta gaa<br>Ala Glu Ile Asn Ile Asp Met Val Leu Gln Asn Val Ser Ser Val Glu<br>290                 295                 300 | 912 |
| gac ggc acc acc gac atc atc ttc acc tgc cct cgt tcc gac ggc cgc<br>Asp Gly Thr Thr Asp Ile Ile Phe Thr Cys Pro Arg Ser Asp Gly Arg | 960 |

```
                305                 310                 315                 320
cgc gcg atg gag atc ttg aag aag ctt cag gtt cag ggc aac tgg acc            1008
Arg Ala Met Glu Ile Leu Lys Lys Leu Gln Val Gln Gly Asn Trp Thr
                    325                 330                 335 aat gtg ctt tac gac gac cag gtc ggc aaa gtc tcc ctc gtg ggt gct            1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg            1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt            1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca            1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat            1248
Leu His Glu Gln Phe Gln Leu Gly Gly Glu Asp Glu Ala Val Val Tyr
                405                 410                 415 gca ggc acc gga cgc                                                        1263
Ala Gly Thr Gly Arg
            420

<210> SEQ ID NO 18
<211> LENGTH: 421
<212> TYPE: PRT
<213> ORGANISM: Corynebacterium glutamicum

<400> SEQUENCE: 18

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220
```

```
-continued

Val Pro Leu Arg Val Arg Ser Ser Tyr Ser Asn Asp Pro Gly Thr Leu
225             230             235             240

Ile Ala Gly Ser Met Glu Asp Ile Pro Val Glu Glu Ala Val Leu Thr
            245             250             255

Gly Val Ala Thr Asp Lys Ser Glu Ala Lys Val Thr Val Leu Gly Ile
            260             265             270

Ser Asp Lys Pro Gly Glu Ala Ala Lys Val Phe Arg Ala Leu Ala Asp
        275             280             285

Ala Glu Ile Asn Ile Asp Met Val Leu Gln Asn Val Ser Ser Val Glu
    290             295             300

Asp Gly Thr Thr Asp Ile Ile Phe Thr Cys Pro Arg Ser Asp Gly Arg
305             310             315             320

Arg Ala Met Glu Ile Leu Lys Lys Leu Gln Val Gln Gly Asn Trp Thr
            325             330             335

Asn Val Leu Tyr Asp Asp Gln Val Gly Lys Val Ser Leu Val Gly Ala
            340             345             350

Gly Met Lys Ser His Pro Gly Val Thr Ala Glu Phe Met Glu Ala Leu
            355             360             365

Arg Asp Val Asn Val Asn Ile Glu Leu Ile Ser Thr Ser Glu Ile Arg
        370             375             380

Ile Ser Val Leu Ile Arg Glu Asp Asp Leu Asp Ala Ala Ala Arg Ala
385             390             395             400

Leu His Glu Gln Phe Gln Leu Gly Gly Glu Asp Glu Ala Val Val Tyr
            405             410             415

Ala Gly Thr Gly Arg
            420
```

DESENSITIZED ASPARTOKINASE

This application is a US national stage 371 filing of PCT/JP00/02456 filed Apr. 14, 2000 and also claims benefit of priority to Japan 11/110437 filed Apr. 19, 1999.

FIELD OF THE INVENTION

The present invention relates to a novel aspartokinase derived from a Coryneform bacterium; a DNA encoding said enzyme; a recombinant DNA containing said DNA; a Coryneform bacterium having said recombinant DNA or a Coryneform bacterium having said DNA on its chromosome; and a process for producing L-lysine by culturing said microorganism.

BACKGROUND OF THE INVENTION

The following processes are known as processes for producing L-lysine by fermentation using a microorganism belonging to the genus *Corynebacterium*:

(1) As for processes which use mutants producing L-lysine, those using an S-(2-aminoethyl)-cysteine (hereinafter abbreviated to as "AEC") resistant mutant [*Amino Acid Fermentation* (*Aminosan Hakko*), 1986, p.273, Japan Scientific Societies Press], an L-homoserine-requiring mutant [*Amino Acid Fermentation* (*Aminosan Hakko*), 1986, p.273, Japan Scientific Societies Press], a respiration-inhibitor resistant mutant (Japanese Published Examined Patent Application No. 55114/93), a pyrimidine analog resistant mutant (Japanese Published Unexamined Patent Application No. 88094/84), and a purine analog resistant mutant (Japanese Published Examined Patent Application No. 062199/88) have been known.

(2) As for processes which use recombinant bacteria constructed with gene recombination techniques, there have been disclosed a vector plasmid which is self-replicating in a microorganism belonging to the genus *Corynebacterium* and has a marker which provides a selectable phenotype in the above microorganism, a process for efficiently introducing the vector plasmid, and a process for efficiently producing various L-amino acids including L-lysine by increasing the intracellular copy number of genes involved in the synthesis of the above amino acids using the above vector plasmids (Japanese Published Examined Patent Application No.11959/93, and Japanese Published Examined Patent Application 55155/95).

As for the control of L-lysine biosynthesis, a concerted feedback inhibition by L-lysine and L-threonine against aspartokinase (hereinafter abbreviated to as "AK") which catalyzes the biosynthesis of aspartyl phosphate from L-aspartic acid is well known. It is known that a microorganism belonging to the genus *Corynebacterium* having a gene (hereinafter abbreviated to as "a desensitized AK gene") encoding a mutant AK which has been freed from such a feedback inhibition (hereinafter abbreviated to as "a desensitized AK") secretes L-lysine extracellularly (*Amino Acid Fermentation* (*Aminosan Hakko*), 1986, p.273, Japan Scientific Societies Press). If information of the nucleotide sequence of a mutation is available, a wild type gene can be converted into a mutant gene by utilizing a technique converting a nucleotide sequence into a desired form in a test tube [e.g. a process using a QuickChange Site-Directed Mutagenesis Kit (Stratagene)] with the above information in combination. Recently, the analysis of the above-mentioned desensitized AK gene at the nucleotide sequence level has been reported [Journal of Bacteriology, 175, 4096 (1993); Molecular Microbiology 5, 1197 (1991); Japanese Published Unexamined Patent Application No. 62866/94].

DISCLOSURE OF THE INVENTION

The object of the present invention is to convert AK, a key enzyme for L-lysine biosynthesis in a Coryneform bacterium, into desensitized AK freed from concerted feedback inhibition by L-lysine and L-threonine and feedback inhibition by L-lysine alone so as to be advantageous for the production of L-lysine.

Through intensive studies to find a process for efficiently producing L-lysine with a Coryneform bacterium, the present inventors have found that a strain, which has a desensitized AK freed from both concerted feedback inhibition by L-lysine and L-threonine and feedback inhibition by L-lysine alone, has an excellent ability of producing L-lysine, thereby completing the present invention.

Thus, the present invention relates to the following (1) to (12).

(1) A DNA encoding an aspartokinase derived from a Coryneform bacterium and has an amino acid sequence wherein the amino acid residue at position 311 is substituted by an amino acid other than Thr in the amino acid sequence shown by SEQ ID NO: 18, and which has been freed from the concerted feedback inhibition by L-lysine and L-threonine.

(2) The DNA according to above (1), wherein the DNA has the nucleotide sequence shown by SEQ ID NO: 17.

(3) The DNA according to above (1), wherein the Coryneform bacterium is one which belongs to a genus selected from the group consisting of *Corynebacterium* and *Brevibacterium*.

(4) A recombinant DNA capable of replicating in a Coryneform bacterium, which is obtained by integrating the DNA according to any one of above (1) to (3) into a vector.

(5) A Coryneform bacterium having the DNA according to any one of above (1) to (3) in its chromosome.

(6) A transformant belonging to Coryneform bacterium which has the recombinant DNA according to above (4).

(7) The transformant according to above (6), wherein the transformant is *Corynebacterium glutamicum* Tf-5 (FERM BP-6689).

(8) A process for producing L-lysine, which comprises culturing a microorganism or transformant selected from the Coryneform bacterium according to above (5) and the transformant according to above (6) and (7) in a medium; producing and accumulating L-lysine in a culture; and collecting the L-lysine from said culture.

(9) An aspartokinase encoded by the DNA according to any one of above (1) to (3).

(10) A DNA encoding an aspartokinase derived from a Coryneform bacterium, and which has a nucleotide sequence encoding the amino acid sequence wherein the amino acid residue at position 311 is Thr in the amino acid sequence shown by SEQ ID NO: 18.

(11) The DNA encoding an aspartokinase according to above (10), which has a nucleotide sequence wherein the nucleotide at position 932 is substituted by cytosine in the nucleotide sequence shown by SEQ ID NO: 17.

By using the DNA, a DNA encoding the aspartkinase of the above (1) can be provided.

(12) An aspartokinase encoded by the DNA according to any one of above (10) or (11).

The present invention is described in detail below.

Any microorganism can be applied as a bacterium which provides DNA comprising a gene encoding AK (hereinafter abbreviated to as "an AK gene"), so long as the microorganism belongs to Coryneform bacteria and has an AK activity.

Examples of Coryneform bacteria in the present invention include *Agrococcus, Agromyces, Arthrobacter, Aureobacterium, Brevibacterium, Cellulomonas, Clavibacter, Corynebacterium, Microbacterium, Rathayibacter, Terrabacter* and *Turicella*. Preferred are *Corynebacterium* and *Brevibacterium*. Specific examples include the following strain.

*Corynebacterium glutamicum* ATCC13032, *Corynebacterium glutamicum* ATCC13869, *Corynebacterium glutamicum* ATCC13870, *Corynebacterium callunae* ATCC 15991 and *Corynebacterium acetoglutamicum* ATCC 15806.

A wild type strain provides a wild type AK gene which is subjected to the feedback inhibition by L-lysine, or by both L-lysine and L-threonine. An example of processes for obtaining a desensitized AK gene freed from such feedback inhibition from the wild type AK gene is a process which comprises performing a mutagenized operation on wild type strains [e.g. a process of using N-methyl-N'-nitro-N-nitroso guanidine (NTG), *Microorganism Experiment Manual (Biseibutsu Jikken Manual)*, 1986, p.131, Kodansha Scientific], and obtaining the target gene from mutants which are selected by utilizing AEC resistance as an indicator and has a L-lysine productivity. Preferable mutants include, a L-lysine-producing bacterium obtained from wild type *Corynebacterium glutamicum* ATCC13032 by mutagenized treatment, or a strain comprising a desensitized AK gene which is acquired by obtaining a wild type AK gene, inducing mutagenesis to the gene by the above NTG method or in vitro mutagenized techniques (e.g. a process of using hydroxylamine, *Molecular and General Genetics*, 145, 101 (1978)), and desensitizing it with AEC resistance and L-lysine productivity as indicators.

An AK gene can be isolated from strains comprising AK genes by, for example, the method of Saitoh et al. [*Biochimica et Biophysica Acta*, 72, 619 (1963)]. That is, a chromosomal DNA is prepared and then cleaved with an appropriate restriction enzyme. After cleavage, the obtained cleaved fragment is ligated to a vector (e.g. a plasmid) capable of self-replicating in a microorganism, followed by introduction into a host microorganism having no AK activity. A transformant expressing AK activity is selected from the microorganism, and then the target gene is obtained by isolation from the transformant.

Any microorganism can be used as a host microorganism, so long as an AK gene of Coryneform bacteria can be expressed in the microorganism. A preferred one is an AK defective strain of *Escherichia coli*.

Any vector can be used as a vector capable of self-replicating, so long as it can self-replicate in the microorganism into which the vector is introduced. Examples include vectors capable of self-replicating in *Escherichia coli* such as pUC18 (produced by Takara Shuzo Co., Ltd.) and pBluescriptSK(−) (produced by Toyobo Co., Ltd.) and shuttle vectors capable of self-replicating both in *Escherichia coli* and in Coryneform bacteria such as pCE54 (Japanese Published Unexamined Patent Application No. 105999/83).

The ligation of a vector to a DNA fragment containing an AK gene can be carried out by an ordinary method of using T4DNA ligase and the like.

The introduction into a host can be carried out by the method of Hanahan et al. [*Journal of Molecular Biology*, 166, 557 (1983)] in the case where the host is *Escherichia coli*.

Furthermore, an AK gene can also be isolated by the following process.

Oligomeric DNA are synthesized based on the nucleotide sequence information of the known AK gene derived from *Corynebacterium glutamicum* [e.g. GenBank Accession No. E06825]. By using the DNA as a primer, a DNA fragment comprising the gene is then amplified by PCR and is isolated. The DNA fragment is ligated to a vector containing a selective marker gene, and is then introduced into an appropriate host microorganism such as *Escherichia coli* and Coryneform bacteria. An AK gene can be obtained by isolating the introduced vector from the microorganism. In this case, an AK defective strain is not necessarily used as a host microorganism.

Any vector can be applied as a vector used to prepare "the recombinant DNA capable of replicating in a Coryneform bacterium" of the present invention, so long as it is capable of self-replicating in a Coryneform bacterium. Specific examples include pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCG11 (Japanese Published Unexamined Patent Application No. 134500/82), pCG116, pCE54 and pCB101 (each disclosed in Japanese Published Unexamined Patent Application No. 105999/83), pCE51, pCE52 and pCE53 [*Molecular and General Genetics*, 196, 175 (1984)], pCS299P of which production process is described in the present invention, and the like. Preferably, vectors such as pCG116 and pCS299P, i.e., relatively small sized vectors having a large number of cloning sites and a selective marker gene such as a drug-resistant gene, are used.

Examples of methods for introducing the above recombinant DNA into a Coryneform bacterium include protoplast method [e.g. Japanese Published Unexamined Patent Application Nos. 186492/82 and 18649/82] and electroporation [e.g. *Journal of Bacteriology*, 175, 4096 (1993)].

Any Coryneform bacterium can be used as a coryne bacterium having a DNA encoding the novel AK gene of the present invention on its chromosome, so long as the bacterium has the AK gene on its chromosome. Examples include a strain obtained by mutagenized operation; and a microorganism where the above DNA fragment is artificially inserted into its chromosome by homologous recombination [*Bio/Technology*, 9, 84 (1991)], methods of using a phage or transposon (*Escherichia coli* and *Salmonella typhimurium*, 1996, p.2325 and p.2339, American Society for Microbiology) and the like.

By culturing the thus obtained transformant belonging to Coryneform bacteria which has a DNA comprising the novel AK gene, L-lysine can be produced and accumulated in a culture.

As a medium for culture, there can be used a common nutritive medium containing a carbon source, a nitrogen source, inorganic salts and the like.

Examples of carbon sources include saccharides such as glucose, fructose, sucrose, maltose and starch hydrolysate; alcohols such as ethanol; and organic acids such as acetic acid, lactic acid and succinic acid.

Examples of nitrogen sources include various types of inorganic and organic ammonium salts such as ammonia, ammonium chloride, ammonium sulfate, ammonium carbonate and ammonium acetate; nitrogen-containing compounds such as urea or others; and nitrogen-containing organic substances such as meat extract, yeast extract, corn steep liquor and soybean hydrolysate.

Examples of inorganic salts to be used include potassium dihydrogen phosphate, dipotassium hydrogen phosphate, ammonium sulfate, sodium chloride, magnesium sulfate and calcium carbonate.

In addition, trace nutritive sources such as biotin and thiamine can be added as appropriate. Additives for a medium such as meat extract, yeast extract, corn steep liquor and casamino acid may be used instead of these trace nutritive sources.

Culturing is carried out under aerobic conditions, such as a shaking culturing and a submerged-aerated-agitated culturing. Generally, the culturing temperature is preferably 20 to 40° C. The pH of the medium is preferably maintained around neutral. The regulation of pH is carried out using inorganic or organic acid, an alkaline solution, urea, calcium carbonate, ammonia and the like. The culturing period is usually for 1 to 6 days.

After completion of the culture, cells are removed. L-lysine can be collected from the obtained culture by known methods such as activated carbon treatment and ion exchange resin treatment.

The present invention is further described in the following examples. The present invention is not limited to these examples.

BRIEF DESCRIPTION OF THE DRAWING

FIG. 1 is an illustration of a process for constructing pCS299P.

BEST MODE FOR CARRYING OUT THE INVENTION

EXAMPLE 1

Construction of Plasmid pCS299P

Figure 1:
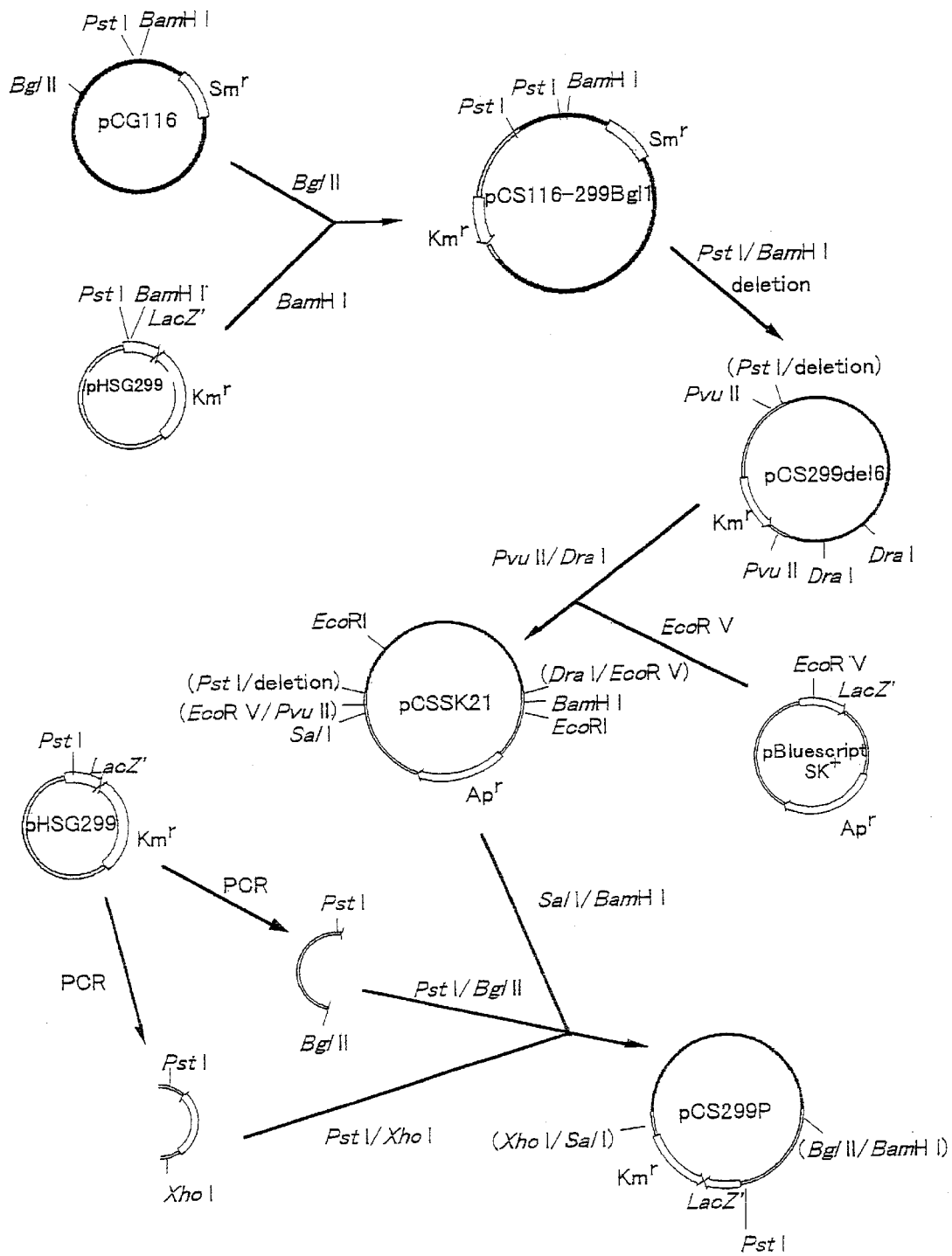
FIG. 1.

Shuttle plasmid pCS299P capable of self-replication in both E. coli and Coryneform bacteria was constructed as follows.

pCG116 [Bio/Technology, 11, 921 (1993)] was cleaved with BglII (produced by Takara Shuzo Co., Ltd.) to give a BglII-cleaved fragment.

After pHSG299 (produced by Takara Shuzo Co., Ltd.) was cleaved with BamHI (produced by Takara Shuzo Co., Ltd.), the resulting BamHI-cleaved fragment was concentrated by ethanol precipitation according to a general method, and then treated with alkaline phosphatase. The thus obtained two fragments were mixed together and subjected to a ligase reaction using a Ligation Kit Ver. 1 (produced by Takara Shuzo Co., Ltd.). The reaction product was used to transform E. coli NM522 according to a standard protocol [Molecular Cloning, Second Edition, 1989, Cold Spring Harbor Laboratory Press (hereinafter, referred to as "Molecular Cloning, $2^{nd}$ Ed.")]. The strain was cultured on LB agar medium containing 20 μg/ml kanamycin [10 g of Bactotrypton (produced by Difco), 5 g of yeast extract (produced by Difco), 10 g of sodium chloride and 16 g of Bactoagar (produced by Difco) per liter of water, adjusted to pH 7.0], thereby selecting transformants. The transformants were cultured overnight in LB medium containing 20 μg/ml kanamycin, and then plasmids were prepared from the obtained culture by the alkaline SDS method (Molecular Cloning, $2^{nd}$ Ed.), thereby obtaining pCS116-299BglI DNA.

Restriction enzyme cleavage sites of the resulting pCS116-299BglI were confirmed in a general manner.

The pCS116-299BglI DNA was used to transform Corynebacterium ammoniagenes strain ATCC6872 by electroporation [FEMS Microbiology Letters, 65, 299, (1989)].

The strains were cultured on CM agar medium containing 20 μg/ml kanamycin [10 g of Polypeptone S (produced by Nihon Pharmaceutical Co., Ltd.), 5 g of Yeast Extract S (produced by Nihon Pharmaceutical Co., Ltd.), 10 g of Ehrlich's meat extract (produced by Kyokuto Pharmaceutical Industrial Co., Ltd.), 3 g of sodium chloride and 30 μg of biotin per liter of water, adjusted to pH 7.2], thereby selecting transformants. The transformants were treated in a general method to extract plasmids, which were then cleaved with restriction enzymes to confirm that the plasmid was pCS 116-299BglI.

The pCS116-299BglI DNA was cleaved with PstI (produced by Takara Shuzo Co., Ltd.) and BamHI and then purified by ethanol precipitation. Partially deleted plasmids were obtained from the resulting DNA using a Kilo-Sequencing Deletion Kit (produced by Takara Shuzo Co., Ltd.). Each of the plasmids was used to transform E. coli strain NM522 in a general manner. The strains were cultured on LB agar medium containing 20 μg/ml kanamycin to select transformants. The transformants were cultured overnight in LB medium containing 20 μg/ml kanamycin, and then plasmids were prepared from the obtained culture by the alkaline SDS method. According to standard protocols, a restriction enzyme map for each plasmid was created to select a series of partially deleted plasmids of different deletion lengths.

Each of the selected plasmids was used to transform Corynebacterium ammoniagenes ATCC6872 by electroporation. The resulting transformants were inoculated onto CM agar medium containing 20 μg/ml kanamycin, and then cultured at 30° C. for 2 days to select a plasmid capable of self-replication in Corynebacterium ammoniagenes by utilizing the presence or absence of developed colonies resistant to kanamycin as an indicator.

From among the plasmids capable of self-replication, a plasmid having the longest deletion region was selected and designated pCS299de16.

The pCS299de16 DNA was prepared from the transformant in a general manner, and then cleaved with restriction enzymes DraI and PvuII (each produced by Takara Shuzo Co., Ltd.). The cleaved DNA fragments were fractionated by agarose gel electrophoresis to isolate a DNA fragment of approximately 2.7 kb having a pCG16-derived DNA, which was then extracted and purified using a DNA Prep Kit (produced by Asahi Glass Company).

pBluescript SK(+)(produced by Toyobo Co., Ltd.) DNA was cleaved with EcoRV (produced by Takara Shuzo Co., Ltd.) in a general manner. The resulting cleaved DNA fragments were concentrated by ethanol precipitation and then treated with alkaline phosphatase. The thus treated DNA fragments were fractionated by agarose gel electrophoresis, followed by extraction and purification using a DNA Prep Kit.

After the above 2.7 kb fragment and the pBluescript SK(+) fragment were ligated using a Ligation Kit Ver. 1, the ligated DNA was used to transform E. coli strain NM522 in a general manner. The strains were cultured on LB agar medium containing 100 μg/ml ampicillin, 50 μg/ml X-Gal (5-bromo-4-chloro-3-indoyl-β-D-galactoside) and 1 mmol/l IPTG (isopropylthio-β-D-galacto side), thereby selecting transformants. The transformants were cultured overnight in LB medium containing 100 μg/ml ampicillin, and then plasmids were prepared from the obtained culture by the alkaline SDS method. According to standard protocols, a restriction enzyme map for each plasmid was made. A plasmid which provided 3.4 kb and 2 kb fragments by cleavage with EcoRI was designated pCSSK21.

DNAs shown by SEQ ID NOs: 1 and 2 were synthesized and were used as PCR primers. PCR reaction was carried out using pHSG299DNA as a template and using Taq DNA polymerase (produced by Takara Shuzo Co., Ltd.) under the manufacturer's recommended reaction conditions. The reaction product was precipitated with ethanol in a general method, and then cleaved with restriction enzymes PstI and XhoI (produced by Takara Shuzo Co., Ltd.). The cleaved DNA fragments were fractionated by agarose gel electrophoresis to isolate a DNA fragment of approximately 1.3 kb, which was then extracted and purified using a DNA Prep Kit.

DNAs shown by SEQ ID NOs: 3 and 4 were synthesized and were used as PCR primers. PCR reaction was carried out using pHSG299DNA as a template and using Taq DNA polymerase under the manufacturer's recommended reaction conditions. The reaction product was precipitated with ethanol in a general method, and then cleaved with restriction enzymes PstI and BglII. The cleaved DNA fragments were fractionated by agarose gel electrophoresis to isolate a DNA fragment of approximately 1.3 kb, which was then extracted and purified using a DNA Prep Kit.

The plasmid pCSSK21 obtained above was cleaved with SalI (produced by Takara Shuzo Co., Ltd.) and BamHI. The cleaved DNA fragments were fractionated by agarose gel electrophoresis to isolate a DNA fragment of approximately 2.7 kb, which was then extracted and purified using a DNA Prep Kit. These three extracted and purified DNA fragments were mixed together and ligated using a Ligation Kit Ver. 1.

The ligated DNA fragment was used to transform *E. coli* strain NM522 in a general method. The strain was cultured on LB agar medium containing 20 µg/ml kanamycin, 50 µg/ml X-Gal and 1 mmol/l IPTG, thereby selecting transformants.

The transformants were cultured overnight in LB medium containing 20 µg/ml kanamycin, and then plasmids were prepared from the obtained culture by the alkaline SDS method. According to standard protocols, a restriction enzyme map for each plasmid was created. A plasmid having the structure shown in FIG. 1 was designated pCS299P.

EXAMPLE 2

Generation of L-lysine Producing Mutant and Determination of Nucleotide Sequence of AK Gene Derived Therefrom

*Corynebacterium glutamicum* wild-type strain (ATCC13032) was subjected to NTG mutagenesis (see Experimental Manual for Microorganisms, 1986, p. 131, Kodansha Scientific), and then spread onto a minimal agar medium containing 1 mg/ml AEC and 1 mg/ml L-threonine [5 g of glucose, 0.75 g of dipotassium monohydrogen phosphate, 0.75 g of monopotassium dihydrogen phosphate, 1 g of ammonium sulfate, 0.5 g of magnesium sulfate heptahydrate, 0.1 g of sodium chloride, 10 mg of ferrous sulfate heptahydrate, 8 mg of manganese sulfate heptahydrate, 1 mg of calcium hydrochloride, 1 mg of thiamine hydrochloride, 0.03 mg of biotin and 16 g of agar (produced by Difco) per liter of water, adjusted to pH 7.2], followed by culturing at 30° C. for 2 days. The developed colonies were isolated and tested for their L-lysine productivity by the procedures shown in Example 5 below, thereby selecting clones having improved productivity.

From one of the selected clones (desigated AEC11) and the wild-type strain ATCC13032, AK gene was amplified by PCR as mentioned below, and the nucleotide sequence was determined.

Chromosomal DNA was prepared from each strain by the method of Saitoh et al. [Biochimica et Biophysica Acta, 72, 619 (1963)]. Based on the nucleotide sequence of AK gene known in *Corynebacterium glutamicum* strain ATCC 13869 [GenBank, Accession No. E06825], DNA primers for amplification were designed. The nucleotide sequences of the DNA primers were shown by SEQ ID NOs: 5 and 6. PCR was carried out using the chromosomal DNA prepared above, the DNA primers, Perkin Elmer's Thermal Cycler (GeneAmp PCR System 9600), DNA polymerase derived from *Phyrococcus* sp. KOD (produced by Toyobo Co., Ltd.) and a buffer attached thereto. PCR was repeated for 30 cycles, each cycle of which consists of reactions at 94° C. for 30 seconds, at 60° C. for 30 seconds, and at 74° C. for 60 seconds. An amplified DNA fragment of approximately 1.5 kb was purified using a PCR Product Presequencing Kit (produced by Amersham Pharmacia). The purified DNA was used as a template for cycle sequencing. DNA primers for the sequencing reaction were designed based on the nucleotide sequence of above AK gene. The nucleotide sequences of the DNA primers were shown by SEQ ID NOs: 7 to 16. The cycle sequencing reaction was repeated for 25 cycles using an ABI PRISM Dye Terminator Cycle Sequencing Ready Reaction Kit (manufactured by Perkin Elmer), each cycle of which consists of reactions at 96° C. for 10 seconds, at 50° C. for 5 seconds, and at 60° C. for 4 minutes. The nucleotide sequence was determined using an ABI PRISM 377 DNA Sequencing System (manufactured by Perkin Elmer).

The nucleotide sequence of the mutated AK gene derived from the strain AEC11 and the corresponding amino acid sequence of the open reading frame are shown by SEQ ID NOs: 17 and 18. The nucleotide sequence of the mutated AK gene shown by SEQ ID NO: 17 had thymine at position 932, whereas the wild-type AK gene had cytosine at the same position. This nucleotide substitution resulted in an amino acid replacement of L-threonine residue (codon: ACC) at position 311 in the wild-type AK to isoleucine residue (codon: ATC) in the AEC11-derived AK gene. There are reports of mutations providing a desensitized *Corynebacterium glutamicum* AK gene, such as mutation of Ala279 to any amino acid other than Ala (Japanese Published Unexamined Patent Application Nos. 62866/94 and 261766/94), Gly345Asp [Journal of Bacteriology, 175, 4096 (1993)], Ser301Tyr [Molecular Microbiology, 5, 1197 (1991)], Ser301Phe and Thr308Ile (each of which is described in Japanese Published Unexamined Patent Application No. 261766/94). However, none of these mutations corresponded to the above mutation at position 331.

EXAMPLE 3

Cloning of the Mutated AK Gene and Introduction Thereof Into Coryneform Bacteria Effects of the above mutation on the L-lysine productivity were evaluated as follows.

The AK genes were cloned from each of *Corynebacterium glutamicum* wild-type strain (ATCC13032) and L-lysine producing strain AEC11 by PCR method. A gene fragment of approximately 1.5 kb containing the ATCC 13032- or AEC11-derived AK gene obtained in the same manner as described in Example 2 was treated with SalII and BamHI (produced by Takara Shuzo Co., Ltd.), subjected to agarose gel electrophoresis, excised from the gel, and purified using a Gene Clean Kit (BIO 101). The shuttle vector pCS299P capable of self-replication in both *E. coli* cells and Coryneform bacteria shown by Example 1 was cleaved with SalI and BamHI and then ligated to the above AK gene fragment using a Ligation Kit Ver. 1 (produced by Takara Shuzo Co., Ltd.). The ligated product was used to transform *E. coli* strain DH5 a (produced by Toyobo Co., Ltd.) according to the manufacturer's instructions. Colonies growing on LB agar medium containing 100 μg/ml of ampicillin were isolated. These colonies were cultured to prepare plasmid DNA in the same manner as described in Example 1. The nucleotide sequence was determined according to the procedures shown in Example 2, thereby selecting clones bearing no PCR-based mutation. Among these selected clones, a plasmid carrying the ATCC13032-derived AK gene was designated pAK1, while a plasmid carrying the AEC11-derived AK gene was designated pAK2.

EXAMPLE 4

Enzymatic Analysis of *Corynebacterium glutamicum* Wild-type AK and the Mutated AK The plasmid pAK1, pAK2 or pCS299P was introduced into *Corynebacterium glutamicum* wild-type strain ATCC13032 by electroporation, respectively [FEMS Microbiology Letters, 65, 299 (1989)]. The resulting strains carrying the plasmid pAK1, pAK2 or pCS299P was designated Tf-14, Tf-5 or Tf-21, respectively. These transformants were assayed for their AK activity by the method of Follettie et al. [Journal of Bacteriology, 175, 4096 (1993)].

AK specific activities of crude extracts from the transformants are shown in Table 1.

The strains into which the AK gene-carrying plasmids had been introduced (Tf-14 and Tf-5) were shown to have AK specific activity approximately 6 times greater than the strain containing the vector (Tf-21). Tf-5 was proven to have been freed from not only concerted inhibition by L-lysine and L-threonine, but also feedback inhibition by L-lysine significantly.

Tf-5 was deposited on Apr. 2, 1999 with National Institute of Bioscience and Human-Technology, Agency of Industrial Science and Technology (1-3, Higashi 1-chome, Tsukuba-shi, Ibaraki-ken, Japan) under accession No. FERM BP-6689.

thiamine hydrochloride, 0.1 mg of biotin, 10 mg of calcium pantothenate, 10 mg of ferrous sulfate heptahydrate, 1 mg of zinc sulfate heptahydrate, 20 mg of nicotinic acid and 10 g of calcium carbonate per liter of water, pH 7.2), followed by culturing under shaking at 30° C. for 16 hours.

One ml of the resulting seed culture was inoculated into 10 ml of a main culture medium (200 g of molasses waste, 45 g of ammonium sulfate, 1 g of urea, 0.5 g of monopotassium dihydrogen phosphate, 0.5 g of magnesium sulfate heptahydrate, 0.3 mg of biotin and 30 g of calcium carbonate per liter of water, pH 7.0), followed by culturing under shaking at 30° C. for 72 hours. The plasmid-carrying ratio at the end of the culturing was measured based on the kanamycin-resistance which was a drug resistance marker of the plasmid. Each strain stably carried the plasmid with the ration of almost 100%.

The amount of L-lysine accumulated in the medium was measured by high performance liquid chromatography.

Results were shown in Table 2.

It was shown that the productivity of L-lysine was significantly improved by the introduction of the mutated AK gene of the present invention.

TABLE 2

| Strain | L-lysine production (g/L) |
|---|---|
| Tf-21 | 0.1 |
| Tf-14 | 0.1 |
| Tf-5 | 8.1 |

INDUSTRIAL APPLICABILITY

According to the present invention, the key enzyme for L-lysine biosynthesis in a Coryneform bacterium, AK, can be modified to give a desensitized form that is freed from concerted inhibition by L-lysine and L-threonine and feedback inhibition by lysine alone, and this desensitized AK is useful for L-lysine production.

Sequence Listing Free Text

SEQ ID NO: 1 description of artificial sequence: synthetic DNA

TABLE 1

| | AK specific activity (nmol Aspartyl-hydroxamate/mg protein/min) | | | | | | |
|---|---|---|---|---|---|---|---|
| | Without | L-Lys | | L-Thr | | L-Lys + L-Thr | |
| Strain | addition | 1 mM | 10 mM | 1 mM | 10 mM | 1 mM each | 10 mM each |
| Tf-21 | 2.8 | | | | | | |
| Tf-14 | 17.3 | 16.5 | 9.7 | 23.1 | 24.3 | 4.8 | 1.2 |
| | (100) | (96) | (56) | (133) | (140) | (28) | (7) |
| Tf-5 | 16.7 | 16.7 | 15 | 30.9 | 35.8 | 18.2 | 18.4 |
| | (100) | (100) | (89) | (185) | (215) | (109) | (110) |

* A value in a parenthesis is a relative activity (%) to the specific activity observed without addition, which is set to 100.

EXAMPLE 5

Effects of Mutated AK on L-lysine Productivity in *Corynebacterium glutamicum*

Tf-5, Tf-14 and Tf-21 prepared in Example 4 were cultured and evaluated for their L-lysine productivity.

Each strain was inoculated into 5 ml of a seed medium (50 g of sucrose, 30 g of soybean hydrolysate, 3 g of urea, 20 g of peptone, 20 g of casamino acid, 20 g of meat extract, 0.5 g of magnesium sulfate heptahydrate, 2 g of monopotassium dihydrogen phosphate, 8 g of ammonium sulfate, 1 mg of SEQ ID NO: 2 description of artificial sequence: synthetic DNA SEQ ID NO: 3 description of artificial sequence: synthetic DNA SEQ ID NO: 4 description of artificial sequence: synthetic DNA SEQ ID NO: 5 description of artificial sequence: synthetic DNA SEQ ID NO: 6 description of artificial sequence: synthetic DNA SEQ ID NO: 7 description of artificial sequence: synthetic DNA SEQ ID NO: 8 description of artificial sequence: synthetic DNA SEQ ID NO: 9 description of artificial sequence: synthetic DNA SEQ ID NO: 10 description of artificial sequence: synthetic DNA SEQ ID NO: 11 description of artificial sequence: synthetic DNA SEQ ID NO: 12 description of artificial sequence: synthetic DNA SEQ ID NO: 13 description of artificial sequence: synthetic DNA SEQ ID NO: 14 description of artificial sequence: synthetic DNA SEQ ID NO: 15 description of artificial sequence: synthetic DNA SEQ ID NO: 16 description of artificial sequence: synthetic DNA

What is claimed is:

1. An isolated DNA encoding an aspartokinase derived from a Coryneform bacterium and having an amino acid sequence as shown in SEQ ID NO: 18, with a substitution at position 311 by any amino acid other than Thr and which has been freed from the concerted feedback inhibition by L-lysine and L-threonine.

2. The DNA according to claim 1, wherein, the amino acid sequence set forth by SEQ ID NO: 18 is encoded by SEQ. ID NO: 17.

3. The DNA according to claim 1, wherein the Coryneform bacterium belongs to a genus selected from the group consisting of *Corynebacterium* and *Brevibacterium*.

4. A recombinant DNA capable of replicating in a Coryneform bacterium, which is obtained by integrating the DNA according to any one of claims 1 to 3 into a vector.

5. A Coryneform bacterium having the DNA according to any one of claims 1 to 3 in its chromosome.

6. A transformant belonging to Coryneform bacterium which harbors the recombinant DNA according to claim 4.

7. The transformant according to claim 6, wherein the transformant is *Corynebacterium glutamicum* Tf-5 (FERM BP-6689).

8. A process for producing L-lysine, which comprises:
culturing in a medium a Coryneform bacterium according to claim 5 or a Coryneform transformant harboring DNA according to any of claims 1–3;
producing and accumulating L-lysine in a culture; and
collecting the L-lysine from said culture.

9. An isolated aspartokinase encoded by the DNA according to any one of claims 1 to 3.

10. The DNA encoding an aspartokinase according to any one of claims 1–3, having a nucleotide sequence as shown in SEQ ID NO:17, with a substitution at position 932 by cytosine.

11. An aspartokinase encoded by the DNA according to claim 10.

12. An isolated DNA encoding an aspartokinase having an amino acid sequence as shown in SEQ ID NO: 18.

13. An isolated DNA having a nucleotide sequence as shown in SEQ ID NO:17.

14. A method of producing Coryneform bacterium which has chromosomal DNA encoding an aspartokinase with an amino acid sequence shown by SEQ ID No.18 in which the amino acid at position 311 is substituted by an amino acid other than Thr, the aspartokinase being freed from the concerted feedback inhibition by L-lysine and L-threonine, comprising the steps of (a) to (c):

(a) introducing into Coryneform bacterium a DNA comprising said DNA encoding an aspartokinase having an amino acid shown by SEQ ID NO.18 in which the amino acid at position 311 is substituted by any amino acid other than Thr, or a DNA which comprises a fragment of said DNA encoding aspartokinase activity comprising the codon corresponding to the substituted amino acid residue at the position 311 in SEQ ID NO: 18;

(b) carrying out recombination of the DNA of step (a) and chromosomal DNA of Coryneform bacterium; and (c) selecting Coryneform bacterium transformed with said DNA of step (a).

15. The method of producing Coryneform bacterium according to claim 14, wherein said amino acid at position 311 is Ile.

* * * * *

UNITED STATES PATENT AND TRADEMARK OFFICE
CERTIFICATE OF CORRECTION

PATENT NO.    : 6,893,848 B1
DATED         : May 17, 2005
INVENTOR(S)   : Haruhiko Yokoi et al.

It is certified that error appears in the above-identified patent and that said Letters Patent is hereby corrected as shown below:

Title page,
Item [56], References Cited, FOREIGN PATENT DOCUMENTS, "5-5514" should read -- 5-55114 --.

Column 1,
Lines 22, 48, 52 and 54, "as" should be deleted.

Column 9,
Line 2, "a" should read -- $\alpha$ --.

Column 21,
Line 43, "wherein," should read -- wherein --;
Line 58, "according" should be deleted;
Line 59, should read -- having the recombinant --; and
Lines 64-67, claim 10 should be deleted.

Column 22,
Lines 37-38, claim 11 should be deleted; and
Lines 64-65, "according to claim 14, wherein said amino acid at position 311 is Ile" should read -- which has chromosomal DNA encoding an aspartokinase with an amino acid sequence shown by SEQ ID NO:18, the aspartokinase being freed from the concerted feedback inhibition by L-lysine and L-threonine, comprising the steps of (a) to (c):
    (a) introducing into Coryneform bacterium a DNA comprising said DNA encoding an aspartokinase having an amino acid shown by SEQ ID NO:18 or a DNA which comprises a fragment of said DNA encoding aspartokinase activity;

UNITED STATES PATENT AND TRADEMARK OFFICE
CERTIFICATE OF CORRECTION

PATENT NO.    : 6,893,848 B1
DATED         : May 17, 2005
INVENTOR(S)   : Haruhiko Yokoi et al.

It is certified that error appears in the above-identified patent and that said Letters Patent is hereby corrected as shown below:

<u>Column 22 (cont'd),</u>
     (b) carrying out recombination of the DNA of step (a) and chromosomal DNA of Coryneform bacterium; and
     (c) selecting Coryneform bacterium transformed with said DNA of step (a) --.

Signed and Sealed this

Twenty-fifth Day of October, 2005

JON W. DUDAS
*Director of the United States Patent and Trademark Office*